United States Patent [19]

Rathvon et al.

[11] Patent Number: 4,495,941
[45] Date of Patent: Jan. 29, 1985

[54] CAST MOVING DEVICE

[76] Inventors: Kathryn P. Rathvon; William P. Rathvon, both of 1607 Berkeley Way, Berkeley, Calif. 94703

[21] Appl. No.: 376,859

[22] Filed: May 10, 1982

[51] Int. Cl.³ .............................................. A61F 3/00
[52] U.S. Cl. ..................................... 128/80 G; 128/94
[58] Field of Search .................... 128/80 R, 80 G, 83, 128/82, 94

[56] References Cited

U.S. PATENT DOCUMENTS

| | | | |
|---|---|---|---|
| 2,607,340 | 8/1952 | Anderson | 128/94 |
| 3,739,772 | 6/1973 | Ennis | 128/80 G |
| 4,019,503 | 4/1977 | Smith | 128/94 |
| 4,111,195 | 9/1978 | Neufeld | 128/83 |
| 4,169,468 | 10/1979 | Murphy | 128/94 |

FOREIGN PATENT DOCUMENTS 21773 of 1914 United Kingdom ............. 128/80 G

Primary Examiner—John D. Yasko
Attorney, Agent, or Firm—Townsend and Townsend

[57] ABSTRACT

A cast moving device includes a main line having an inner end attached to a handle and an outer end connected to a flexible connecting strap, the ends of which are attached to a pair of spaced-apart bands mounted about the cast. Releasable attachment strips mounted to the cast and to the handle keeps the handle stored at an accessible position. The connection between the outer end of the main strap and the bands may be a slip or sliding type of connection to ensure that the lifting force is exerted on both of the two bands.

11 Claims, 5 Drawing Figures

U.S. Patent   Jan. 29, 1985   Sheet 1 of 2   4,495,941
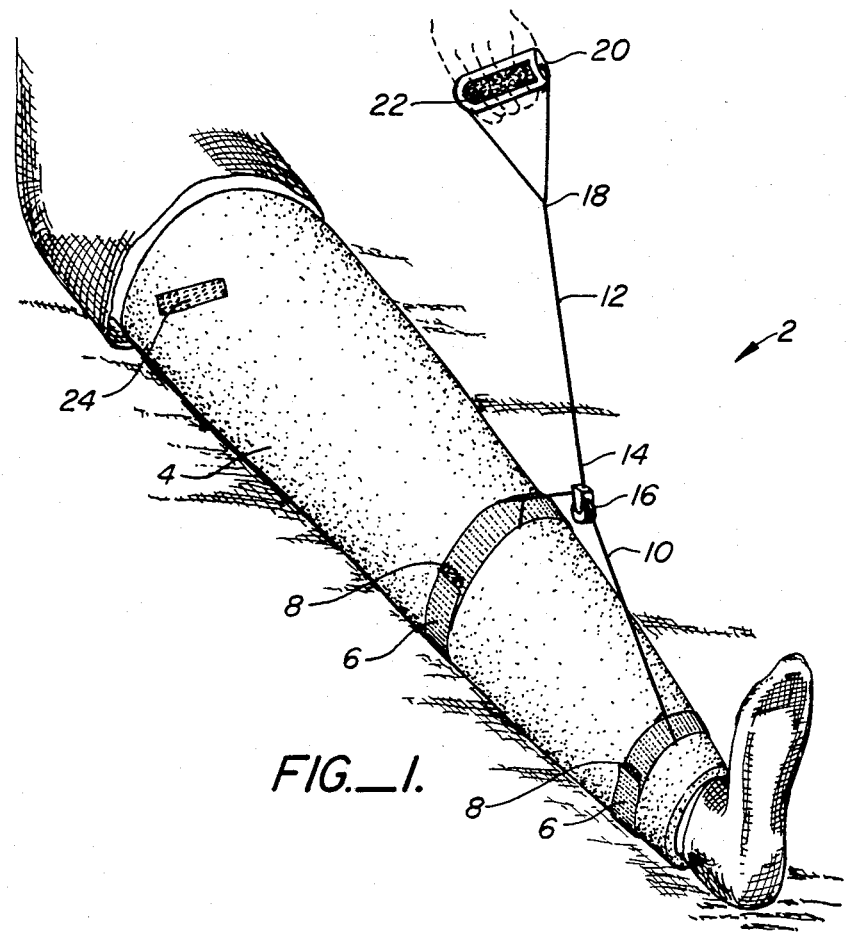
FIG._1.
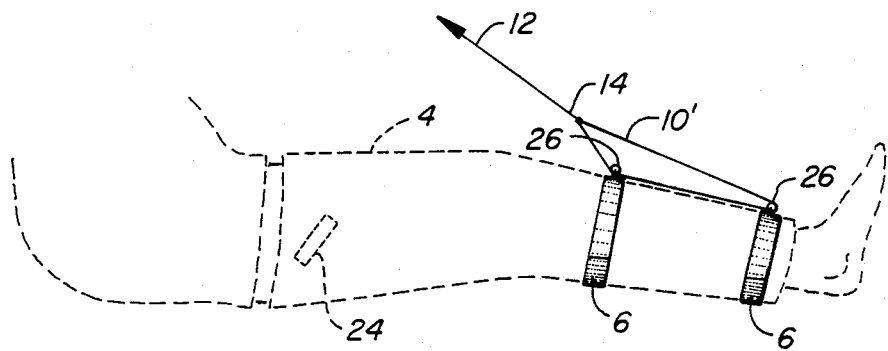
FIG._2.

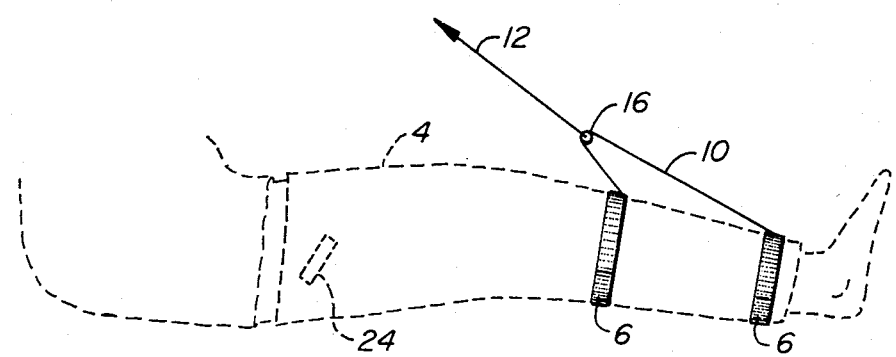
FIG._3.
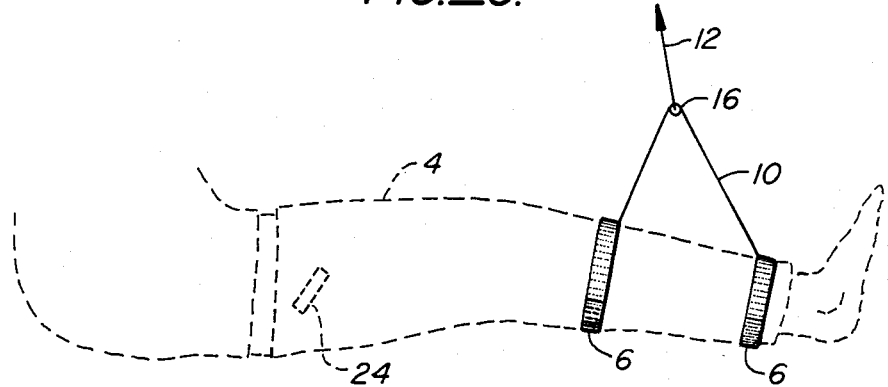
FIG._4.
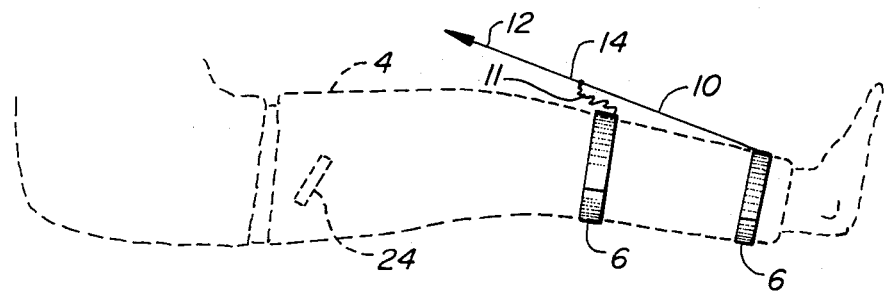
FIG._5.

4,495,941

CAST MOVING DEVICE

DESCRIPTION

BACKGROUND OF THE INVENTION

This invention is related to apparatus which enable a patient to maneuver a relatively immobile leg.

Leg casts are most commonly used to immobilize a patient's leg when the patient has a broken leg bone or after surgery on the leg, typically knee surgery. The weight of the cast, as well as the condition of the patient's leg, makes it difficult, if not impossible, for many patients to re-position their cast encased leg without assistance.

In response to this, apparatus have been developed by which a patient can lift their otherwise immobile leg. The prior art apparatus, exemplified by U.S. Pat. No. 2,183,265, commonly include a sling surrounding the leg. A line or rope is attached at one end to the sling, passes about an overhead pulley, and has a handle for grasping by the user at its other end. The prior art apparatus are often somewhat complicated and require that the user mount a separate overhead pulley to use such apparatus.

SUMMARY OF THE INVENTION

A cast moving device includes a main line attached at its inner end to a handle. One or more bands may be mounted about the cast enclosing the user's leg. When two bands are used a flexible connecting line is connected at its ends to the bands. The outer end of the main line is connected to the flexible connecting line.

Releasable attachment strips (preferably of the type sold under the trademark Velcro), are mounted to the cast and to the handle to retain the handle at a position accessible to the user. Where more than one band is employed, the connection between the outer end of the main line and the band may be a slip or sliding type of connection to ensure that the lifting force is distributed between the bands.

The invention is particularly useful for positioning a cast-enclosed leg. However, it is also useful for positioning a user's leg which is immobilized by a brace or due to a physical disability. In such cases it may be preferred to use at least two bands, rather than a single band, to help distribute the weight of the leg between or among the bands.

A primary feature of the present invention is the provision of releasable attachment strips on the handle and on the cast so that the handle can be retained at a convenient location. Thus the user need not grope around in their bed to find the handle nor is comfort disturbed by an unwelcomed tangle of the main line. Since the device is self-contained, as the user moves from place to place the cast moving device conveniently moves with him or her. No special arrangements need be made, such as mounting an overhead pulley, so user mobility is enhanced.

The user may wrap the main line about the lower end of the cast, near their ankle, and fasten the handle to a band via their respective attachment strips. This allows the handle to be readily accessible when the user is fully clothed and moving about.

Another feature of the invention is the provision of a slip or sliding coupling between the main line and the bands. In one embodiment the connecting line has its two ends fixed to the bands circumscribing the cast. The outer end of the main line is coupled to the connecting line via a roller ensuring that the force exerted by the user on the handle is transmitted to both bands rather than just one as may occur if the main line is attached at a fixed point along the connecting line. In a second embodiment the connecting line is in the form of a loop passing through rings mounted to each band. This likewise ensures that the main line, coupled to the connecting line either in a fixed or a slidable manner, applies the lifting force to both bands.

Other features and advantages of the present invention will appear from the following description in which the preferred embodiments have been set forth in detail in conjunction with the accompanying drawings.

BRIEF DESCRIPTION OF THE DRAWINGS

FIG. 1 is an overall view of a first embodiment of the present invention.

FIG. 2 is a simplified side view of an alternative embodiment of the invention showing a loop type connecting strap.

FIGS. 3 and 4 are simplified side views of the embodiment of FIG. 1 showing the shape of the connecting line when the main line is pulled in different directions.

FIG. 5 is a simplified side view showing the effect of fixing the outer end of the main line to the connecting line of FIG. 1.

DETAILED DESCRIPTION OF THE PREFERRED EMBODIMENTS

Referring now to FIG. 1, the cast moving device 2 of the invention is shown mounted to a cast 4 on the user's leg. Device 2 includes a pair of support loops 6 wrapped about the cast 4 at the outer end of the cast. The loops are preferably coupled at their outer ends using strips of Velcro attachment material 8.

A flexible connecting line 10 is attached at its ends to loops 6. A main line 12 is movably connected at its outer end 14 to connecting line 10 by a roller 16. The inner end 18 of line 12 is connected to a handle 20 sized for grasping by the user. Handle 20 and cast 4 have Velcro attachment strips 22, 24 mounted to them. Attachment strip 24 is mounted to cast 4 at a suitable position to allow the handle to be easily grasped by the user.

The use of a movable or slidable attachment between outer end 14 of main line 12 and connecting line 10, in this case roller 16, ensures that regardless of the angle at which the user pulls on main line 12, both loops 6 will exert a lifting force on cast 4. This is illustrated in FIGS. 3 and 4 which show that as the angle at which main line 12 is pulled changes, the position of roller 16 along connecting line 10 changes so that line 10 remains taut over its entire length.

FIG. 5 illustrates the result of attaching outer end 14 of main line 12 to a fixed position along connecting line 10. In the illustrated example, due to the angle at which main line 12 is pulled, segment 11 of line 10 is slack so all the lifting force is exerted on the outer of the two loops 6. This problem is eliminated by providing a movable or sliding connection between connecting line 10 and main line 12 as in FIGS. 1, 3 and 4.

FIG. 2 discloses another way to ensure that lifting force is exerted on both loops 6. In this case connecting line 10' is a loop passing through circular eyes 26 mounted to support loops 6. This allows the connection between lines 10' and 12 to be fixed because the length of each portion of connecting portion 10' between outer end 14 and eyes 26 varies depending upon the angle at which main line 12 is pulled. If desired a sliding connection between the lines could be used as well.

In use the user secures loops 6 around the cast at two spaced-apart locations. To retain handle 20 when device 2 is not in use, attachment strip 22, mounted to handle 20, is placed against attachment strip 24. This ensures that the handle is conveniently located for grasping by the user. When the user wants to move their relatively immobile cast enclosed leg, handle 20 is removed from attachment strip 24 and raised to lift loops 6 and cast 4 therewith. After the cast is repositioned, handle 20 is again secured via attachment strips 22, 24.

Modification and variation can be made to the disclosed embodiments without departing from the subject of the invention as defined in the following claims. For example, eye bolts could be mounted directly to the cast when the cast is made to make loops 6 unnecessary.

We claim:

1. A limb maneuvering device for use in positioning a limb of a user comprising:
    a flexible line having inner and outer ends;
    a cast surrounding the limb;
    means for coupling said outer end to said cast;
    a handle mounted to said inner end by which the user can position their limb by manipulating said handle; and
    means for releasably attaching said handle to a chosen point on said cast, said chosen point within reach of the user.

2. The limb maneuvering device of claim 1 wherein said limb surrounding means includes first and second attachment points spaced apart along the limb and a connecting member between said attachment points, said outer end coupled to said connecting member.

3. The limb maneuvering device of claim 2 wherein said connecting member is flexible.

4. The limb maneuvering device of claim: 3 wherein said coupling means includes means for slidably coupling said outer end to said flexible connecting member thereby insuring that the force exerted by the user on the handle is applied to said attachment points.

5. The limb maneuvering device of claim 1 wherein said surrounding means includes a leg cast and said handle attaching means includes means for releasably fastening said handle to a first attachment point at an upper end of said cast.

6. The limb maneuvering device of claim 5 wherein said releasably fastening means includes a first mounting element on said cast and a second mounting element on said handle.

7. A limb maneuvering device for use in combination with a cast on a leg of a user to position the cast enclosed leg of the user comprising:
    a band circumscribing the cast;
    a flexible line having inner and outer ends;
    means for coupling said outer end to said band;
    a handle mounted to said inner end of said line; and
    means for releasably attaching said handle to a chosen point on the cast, said chosen point selected to be within the user's reach so that the user can position said cast enclosed leg by grasping said handle, disengaging said handle from the cast and manipulating said handle to move said cast enclosed leg.

8. The limb maneuvering device of claim 7 further comprising means for slidably coupling said outer end and said bands to ensure that the force exerted by the user on the handle is transmitted to both said bands.

9. The limb maneuvering device of claim 9 wherein said releasable fastening means includes a second attachment point at a lower end of said cast.

10. A limb maneuvering device for use in positioning a limb of a user comprising:
    a flexible line having inner and outer ends;
    means for at least partially surrounding the limb including first and second bands circumscribing the limb and spaced apart along the limb;
    means for movably coupling said outer end to said first and second bands;
    a handle mounted to said inner end by which the user can position their limb by manipulating said handle; and
    means for releasably attaching said handle to a chosen point on said surrounding means, said chosen point within reach of the user.

11. The limb maneuvering device of claim 10 wherein said outer end coupling means includes a flexible coupling member connecting said bands and said moveable coupling means includes means for slidably attaching said outer end to said flexible coupling member.

* * * * *